United States Patent [19]

Dementiev et al.

[11] 4,144,444

[45] Mar. 13, 1979

[54] METHOD OF HEATING GAS AND ELECTRIC ARC PLASMOCHEMICAL REACTOR REALIZING SAME

[76] Inventors: Valentin V. Dementiev, Voiskovoi pereulok, 13, kv. 6; Anatoly I. Zhidovich, Leninsky prospekt, 72a, kv. 109; Alfred L. Mosse, Leninsky prospekt, 72a, kv. 66; Oleg I. Yasko, ulitsa Kalinovskogo, 73, korpus 2, kv. 5, all of Minsk; Lev S. Polak, ulitsa Obrucheva, 18, kv. 22, Moscow; Genrikh V. Gulyaev, ulitsa Obrucheva, 16, kv. 103, Moscow; Rafail I. Levenzon, ulitsa Krasikova, 17, kv. 39, Moscow; Nikolai L. Volodin, Revoljutsionnaya ulitsa, 7, kv. 12, Sterlitamak; Filipp B. Vurzel, Bolotnikovskaya ulitsa, 38, korpus 6, kv. 40, Moscow; Alexandr N. Laktjushin, ulitsa Zakharova, 40, kv. 25, Minsk, all of U.S.S.R.

[21] Appl. No.: 560,235

[22] Filed: Mar. 20, 1975

[51] Int. Cl.² ........................ H05B 7/18; B01K 1/00; B23K 9/00
[52] U.S. Cl. .................................... 219/383; 204/170; 219/121 P
[58] Field of Search ............................ 219/383, 121 P; 313/231.3, 231.4; 204/171, 170; 13/2 P, 9 R, 31

[56] References Cited

U.S. PATENT DOCUMENTS

| 3,468,632 | 9/1969 | Gunnell et al. | 219/383 X |
| 3,832,519 | 8/1974 | Wolf et al. | 219/383 X |

*Primary Examiner*—J. V. Truhe
*Assistant Examiner*—Fred E. Bell
*Attorney, Agent, or Firm*—Haseltine, Lake & Waters

[57] ABSTRACT

A method of heating a gas, particularly a chemically reactant ionized gas, designed, in particular, for producing lower olefins and industrial hydrogen from hydrocarbon stock, wherein the gas is mixed with an intermediate heat carrier gas plasma jet and heated additionally with a rotary electric arc.

8 Claims, 12 Drawing Figures

METHOD OF HEATING GAS AND ELECTRIC ARC PLASMOCHEMICAL REACTOR REALIZING SAME

FIELD OF THE INVENTION

The present invention relates to the field of heating gases by an electric discharge to an ionized state, especially chemically reactive ionized gases, and, more particularly, to methods of heating a gas; it may be advantageously employed for the production of lower olefins and industrial hydrogen from hydrocarbon stocks.

PRIOR ART

It is known in the art to employ a variety of methods for manufacturing products at high temperatures from chemically reactive gases by use of an electric arc as the source of heat. Of these one of the most popular methods comprises heating a gas by a high-pressure arc arcing in a longitudinal rotary jet of the gas being heated. An example of practice of this method is natural gas pyrolysis in an electric arc to produce acetylene. One advantage of this method is a high intensity of the electric arc, of the order of several thousand volts, affording a possibility of building a heavy-duty apparatus having relatively low current ratings, of the order of hundreds of amperes. Such an apparatus is fairly simple in design and offers an advantage of a long electrode service life (hundreds of hours), which makes for its reliability and ease of handling under industrial conditions.

However, the longitudinal rotary jet principle of blowing suffers from a serious disadvantage, viz. a considerable temperature gradient across the section of the passage through which gas is blown, with the result that the chemical reactions in the gas jet through the arc column proceed at a far higher rate than those in the jet proximate to the passage walls. These jets are inadequately mixed so that the reactions in different jet zones exhibit a substantial rate differential, largely detracting from the heating effect where heating is accompanied by a chemical reaction.

Thus, for instance, in the pyrolysis of natural gas, there is a large quantity of unreacted methane left in the exterior zones, whereas in the interior zones the product acetylene has time enough to decompose to carbon black. In addition, acetylene homologs are formed. All these factors combine to reduce the efficiency of raw material utilization and boost the cost of the desired product.

It is likewise known in the art to heat gas by use of a rotary electric arc which gives a more uniform pattern of heating. According to this latter method, an electric arc is energized across the electrodes - a central rod-type cathode and an external cooled anode formed as a hollow metallic cylinder. The electric arc is rotated at several thousand revolutions per second by a magnetic field which is set up by a solenoid disposed on the hollow cylindrical anode. A natural gas which is required to be heated is blown axially along the electrodes, heated and mixed by the rotary electric arc. The chemical reactions through the entire volume of gas proceed more uniformly than in the previously described case, so that the rate of methane conversion to acetylene is higher and the desired product is cheaper. However, the voltage across the electric arc in the latter case is one order of magnitude lower. Hence, the capacity of the apparatus can only be raised by stepping up current ratings, with the consequent reduction of the length of electrode service life.

It is further known to heat a gas by use of an intermediate gaseous heat carrier at a high electric arc voltage, obtaining a sufficiently uniform distribution of heat through the volume of the stock. In this method, the intermediate heat carrier gas (e.g. hydrogen or an inert gas as in the pyrolysis of hydrocarbons) is heated by a high-voltage longitudinally-blown electric arc, and the stock gas is fed into the plasma jet at the outlet of the electric-arc plasmochemical reactor of the plasmotron. A process of hydrocarbon pyrolysis according to such a method has been patented in the U.S.A.

This method, however, has a disadvantage which consists in that the intermediate heat carrier gas fails to transfer all its energy to the gas stock being heated: a considerable amount of energy is carried away by the heat carrier to be partially lost in the process of waste-heat recovery. Furthermore, the intermediate heat carrier gas has to be heated to higher temperatures than those needed to trigger and maintain the reaction, which adversely affects the apparatus efficiency, the overheating being the higher the smaller is the amount of heat carrier used, and the quantity of heat carrier has to be kept at a minimum is rarefaction of the reaction products to undesirable levels is to be avoided.

There exist various modifications of the foregoing methods relating to the design of the electric-arc plasmochemical reactor of the plasmotron and the quenching chamber. Thus, for example, U.S. companies offer a range of plasmotron designs with an electric arc rotating between annular electrodes, wherein, as distinct from the plasmotrons with concentric electrodes, both electrodes have an identical surface area covered by the running arc spot. The plasmotron design envisages the provision of several inlets for the stock and quenching gases (liquids) with a view to optimizing the chemical process.

The modernized designs also provide for several additional gas and liquid inlets in order that prequenching with heavier hydrocarbons than the basic stock may be possible, thus improving the efficiency of the process.

A high-current plasmotron has been developed for the pyrolysis of hydrocarbons in a hydrogen plasma jet. In this plasmotron, hydrogen is heated in a three-phase electric-arc plasmotron with graphite electrodes. The plasmotron is also provided with a number of inlets for an intermediate heat carrier gas, for the stock gas to be heated and for a quenching medium.

Also known are electric-arc plasmochemical reactors comprising two electrodes coupled to a source of power, at least one of said electrodes being a hollow cylindrical member, one hollow cylindrical diaphragm of a diameter smaller than that of the hollow cylindrical electrode, one end of said diaphragm adjoining the hollow cylindrical electrode, inlet means for supplying an intermediate heat carrier gas disposed at the other end of said diaphragm, and at least one inlet means for supplying the stock gas to be heated.

The various mentioned improvements, though raising the effectiveness of the devices realizing the aforedescribed methods, still fail to obviate the foregoing serious disadvantages of the methods and installations discussed hereinabove.

SUMMARYS OF THE INVENTION

It is an object of the present invention to provide a method of heating a gas and an electric-arc plasmochemical reactor embodying same, which provides for the heating of gas by a high-voltage electric arc with a sufficiently uniform distribution of heat through the volume of the stock gas being heated across the section of the reaction chamber passage and avoiding substantial overheating of the intermediate heat carrier gas.

The above objective is attained by a method of heating a gas by mixing it with an intermediate heat carrier gas plasma and jet, in accordance with the invention, by stirring the stock gas to be heated with the intermediate heat carrier gas and by effecting additional heating with a rotary electric arc.

It is expedient that the plasma jet be produced by heating the intermediate heat carrier gas with an electric arc connected in series with the rotary electric arc.

It is also desirable that the rotary electric arc and the arc used for heating the intermediate heat carrier gas be combined into a single electric arc.

It is likewise preferred that the electric arc should be rotated by blowing a rotational stream of the intermediate heat carrier gas through the electric arc.

It is no less preferable that the electric arc should be rotated by a swirling jet of the stock gas to be heated.

It is equally preferable that the electric arc should be rotated by a magnetic field.

It is preferred that the terminal portion of the electric arc should be rotated by a magnetic field supplementing the rotational effort of the rotary jet of the intermediate heat carrier gas or that of the swirling jet of the stock gas to be heated.

A preferred intermediate heat carrier gas may be hydrogen, hydrogen chloride, hydrocarbon, a mixture thereof, inert gases, nitrogen, oxygen or water vapor.

It is also preferred that gaseous and/or vaporous hydrocarbons should be employed as the stock gas to be heated.

It is preferred that in an electric-arc plasmochemical reactor realizing the proposed method of heating a gas, comprising two electrodes coupled to a source of power, at least one thereof being formed as a hollow cylinder, one hollow cylindrical diaphragm of a diameter smaller than that of the hollow cylindrical electrode, one end of said hollow cylindrical diaphragm adjoining the hollow cylindrical electrode, inlet means for supplying an intermediate heat carrier gas disposed adjacent the other end of said diaphragm, and at least one inlet means for supplying the stock gas to be heated, in accordance with the invention, the inlet means for supplying the stock gas to be heated should be positioned intermediate the end surfaces of said diaphragm and said hollow cylindrical electrode insulated from said diaphragm.

The proposed method of heating gas affords a possibility of independently controlling the temperature of the intermediate heat carrier gas and the time of its contact with the electric arc by independently adjusting the electric arc current, the consumption rates of the intermediate heat carrier gas and of the stock gas being heated, as well as by controlling the speed of rotation of the electric arc; the same purpose is also achieved through special constructional features of the electric-arc plasmochemical reactor. Thanks to the independent temperature and contact time control feature the gas heating process is optimized, all side reactions are eliminated, and the purity of the desired products is improved.

The rotary electric arc ensures effective mixing of the intermediate heat carrier gas and the stock gas being heated, so that chemical reactions are initiated and proceed in the different-section portions of the electric-arc reactor passage more uniformly as compared with the prior art techniques, thereby raising the rate of conversion of the stock gas being heated to the desired product and reducing its cost.

BRIEF DESCRIPTION OF THE DRAWING

The invention will be better understood from the following detailed description; of some exemplary embodiments thereof taken in conjunction with the accompanying drawings, wherein.

DETAILED DESCRIPTION

Figure 1:
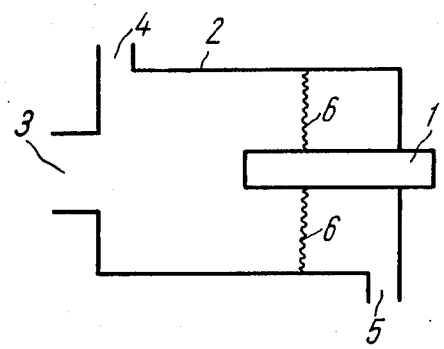
FIG. 1 is a schematic view of a device illustrating the application of the present invention thereto.

The proposed method of heating gas is realized by supplying energy to the stock gas being heated by two sources:

(1) an intermediate heat carrier gas plasma jet heated, for instance, by a longitudinally-blown high-voltage arc;

(2) by the rotary cross-blown electric arc. To obtain an overall size reduction and minimize the losses, the process is effected in a single reactor. The longitudinally-blown electric arc and the cross-blown electric arc, both arcs rotating, are series-connected to form a single arc having a sufficiently long arc column extending along the axis of a small-diameter cylindrical bore and a terminal portion rotating in a larger-diameter bore. The intermediate heat carrier gas serves for longitudinal-rotational blowing of the portion of the arc column disposed in the narrow bore. The stock gas to be heated, is supplied at the point of juncture of the two bores. The stock gas is mixed with the heat carrier gas by the rotating portion of the arc column and receives additional energy therefrom.

This supplementary energy supply from the rotating portion of the arc enables the temperature of the intermediate heat carrier gas to be reduced as against the method of stock pyrolysis in a plasma jet, thereby contributing to a higher operating efficiency of the installation. Besides, owing to the lower initial temperature of the plasma jet, local stock overheating at the initial mixing stage is prevented, permitting a longer reaction time. This is a substantial advantage inasmuch as the mixing and reaction times in the plasma installations are compatible so that a longer reaction time permits a longer mixing section without any damaging consequences for the process. Accordingly, the heat carrier gas is more effectively mixed with the stock gas to be heated, and the latter is more efficiently utilized. The rotating portion of the arc likewise contributes to improved mixing.

The electric arc may be rotated either by supplying the stock gas to be heated in the form of an eddying flow or by use of an external magnetic field, or else by simultaneously employing both mentioned techniques in combination.

The intermediate heat carrier gas may be one of the reactant mixture components least liable to be affected by the non-uniform temperature profile of the arc column or else one requiring a longer swelling time in the high-temperature zone.

Practice of the novel process of this invention may be further understood by reference to the following specific examples.

EXAMPLE 1

The intermediate heat carrier gas is hydrogen; the gas to be heated (parent stock) is natural gas of the following composition: $CH_4 = 77.3$ vol.%; $C_2H_2 = 19.6$ vol.%; $C_3H_8 = 3.14$ vol.%.

Process parameters and consumption coefficients:
1. Current magnitude, 630 amp;
2. Arc power rating, 769 kW;
3. Useful power, 641 kW;
4. Hydrogen consumption, 141 cu.nm/hr;
5. Natural gas consumption, 123 cu.nm/hr;
6. Reaction temperature, 1,750° K.;
7. Composition of pyrolysis gases, vol. %:

|  |  |
|---|---|
| $H_2$ | 76.8 |
| $CH_4$ | 2.53 |
| $C_2H_2$ | 13.64 |
| $C_2H_4$ | 0.46 |
| $CO_2$ | 0.1 |
| $CO$ | 2.27 |
| $N_2$ | 3.03 |
| $C_2H_2$ homologs | 0.47 |

8. Total natural gas conversion, 92.5%;
9. Conversion to acetylene, 81.2%;
10. Specific electric energy consumption disregarding waste-heat recovery, 11.5 kW-hr/cu.nm $C_2H_2$.

EXAMPLE 2

The intermediate heat carrier gas and the gas to be heated (parent stock) are both represented by natural gas of the following composition: $CH_4 = 77.3$ vol.%; $C_2H_6 = 19.6$ vol.%; $C_3H_8 = 3.14$ vol.%.

Process parameters and composition coefficients:
1. Current magnitude, 300 A;
2. Arc power rating, 162 kW;
3. Useful power, 64.3 kW;
4. Overall consumption of the heat carrier and stock gas, 75 cu.nm/hr;
5. Reaction temperature, 1,750° K.;
6. Composition of pyrolysis gas, vol. %:

|  |  |
|---|---|
| $H_2$ | 68.5 |
| $CH_4$ | 6.5 |
| $C_2H_2$ | 17.9 |
| $C_2H_4$ | 0.9 |

7. Total natural gas conversion, 88.6%;
8. Conversion to acetylene, 85.3%;
9. Specific electric energy consumption disregarding waste-heat recovery, 12.0 kW-hr/cu.nm $C_2H_2$.

EXAMPLE 3

The intermediate heat carrier gas is hydrogen; the parent stock to be heated is gasoline fed into the reactor as a vapor at a temperature of 200 to 300° C.

Process parameters and consumption coefficients:
1. Current magnitude, 660 A;
2. Arc power rating, 765 kW;
3. Useful power, 613 kW;
4. Heat carrier consumption, 140 cu.nm/hr;
5. Gasoline consumption, 155 kg/hr;
6. Reaction temperature, 1,650° K.;
7. Composition of pyrolysis gases, vol. %:

|  |  |
|---|---|
| $H_2$ | 68.5 |
| $CH_4$ | 8.2 |
| $C_2H_2$ | 16.5 |
| $C_2H_4$ | 8.2 |
| $CO_2$ | 0.1 |
| $CO$ | 0.7 |
| $N_2$ | 0.8 |
| $C_3H_6$ | 1.2; |

8. Total gasoline conversion, 92.1%;
9. Conversion to ($C_2H_2 + C_2H_4 + C_3H_6$), 80.0%;
10. Specific electric energy consumption disregarding waste-heat recovery, 7.5 kW-hr/kg $C_2H_2+C_2H_4+C_3H_6$.

EXAMPLE 4

The intermediate heat carrier gas is nitrogen; the stock gas to be heated is methane.

Process parameters and consumption coefficients:
1. Current magnitude, 280A;
2. Arc power rating, 170 kW;
3. Useful power, 115 kW;
4. Nitrogen consumption, 72 cu.nm/hr;
5. Natural gas consumption, 180 cu.nm/hr;
6. Composition of pyrolysis gases, vol.%:

|  |  |
|---|---|
| HC | 12.3 |
| $H_2$ | 30.1 |
| $C_2H_2$ | 4.8 |
| $C_2H_6$ | 0.860 |
| $C_2H_4$ | 0.156 |
| $C_3H_8$ | 0.14 |
| $CH_4$ | 31.7; |

7. The degree of conversion of the parent methane stock to the desired products was up to 90 percent.
8. The specific electric energy consumption disregarding waste-heat recovery was 83 kW-hr/kg HCN.

Referring now to FIG. 1, an apparatus realizing the method of the present invention comprises electrodes 1 and 2 connected to a power source (not shown in the drawing), an inlet means 3 for supplying an intermediate carrier gas plasma jet, an inlet means 4 for supplying gas to be heated, and an orifice 5 for releasing the hot gas.

A rotary electric arc 6 is energized across the electrodes 1 and 2.

Figure 2:
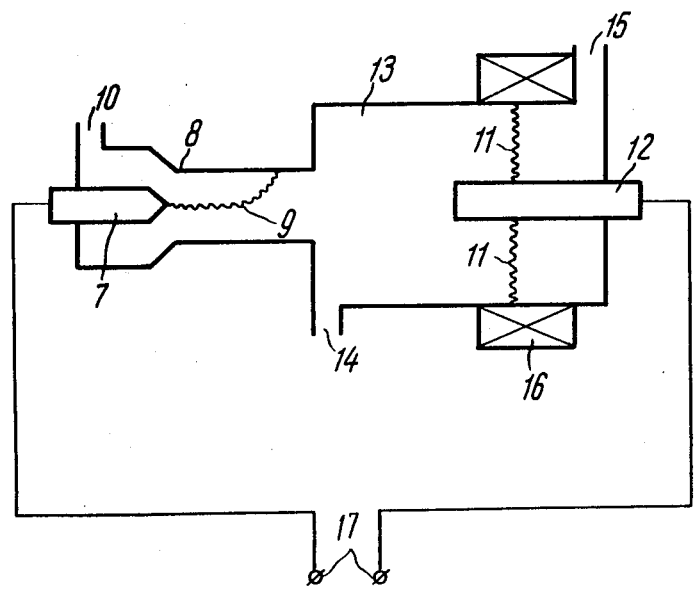
FIG. 2 is a schematic representation of another embodiment of the device.

In another embodiment of the gas heating apparatus, use is made of a rod-type electrode 7 (FIG. 2) and of a hollow cylindrical electrode, with an electrical arc 9 energized between said electrodes for heating an intermediate heat carrier gas delivered through an inlet means 10. Another electric arc 11 is energized across a central electrode 12 and a hollow cylindrical electrode 13. The stock gas is injected through an orifice 14, and the mixture being heated is released through an orifice 15. The electric arcs 9 and 11 are series-connected by virtue of a contact established between the electrodes 8 and 13. The electric arc 11 is revolved by solenoid 16. The electrodes 7 and 12 are connected to terminals 17 of the power source (not shown in the drawing).

Figure 3:
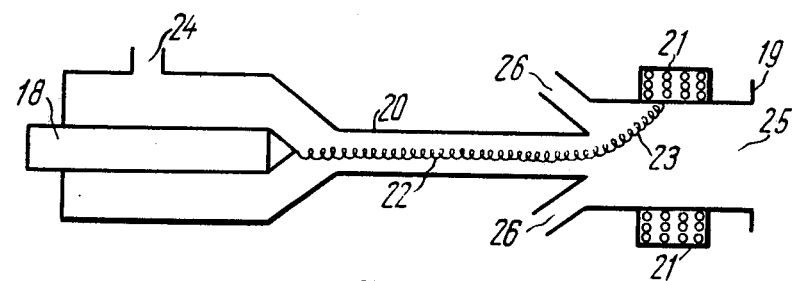
FIG. 3 is a schematic view of still another embodiment of the device.

In an alternative embodiment of a plasmotron-reactor arrangement- (FIG. 3) there are likewise provided a rod-type electrode 18, a hollow cylindrical electrode 19 and a diaphragm 20. The electrode 19 is larger in diameter than the diaphragm 20. A solenoid 21 is disposed on the hollow electrode 19. A longitudinally-blown portion 22 of the electric arc is disposed in the diaphragm 20, whereas a cross-blown arc portion 23 rotating in a magnetic field is disposed in the electrode 19. An orifice 24 serves to inject heat carrier gas, and orifice 25 serves to discharge the heated gas. Inlet means 26 for the stock gas to be heated is disposed intermediate the diaphragm 20 and the electrode 19.

Figure 4:
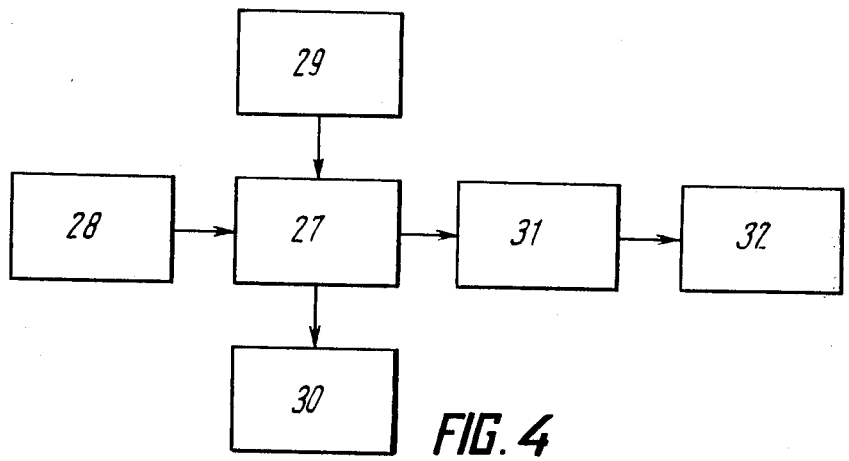
FIG. 4 is a block diagram of a device for heating a gas by means of an electric arc, illustrated in its entirety.

The apparatus for heating a gas illustrated in FIG. 4 comprises an electric-arc plasmochemical reactor (plasmotron) 27, a source of power supply 28 which supplies said plasmotron 27, a source of gas supply 29 which supplies said plasmotron 27 with the intermediate heat carrier gas and with the stock gas to be heated, auxiliary systems 30 (cooling, control and measurement systems) designed to ensure smooth functioning of said plasmotron 27, quenching members 31, wherein the desired product is fixed in the gases heated in said plasmotron 27, and a system 32 for the recovery of the desired product from the gases delivered thereinto from said quenching member 31.

Figure 5:
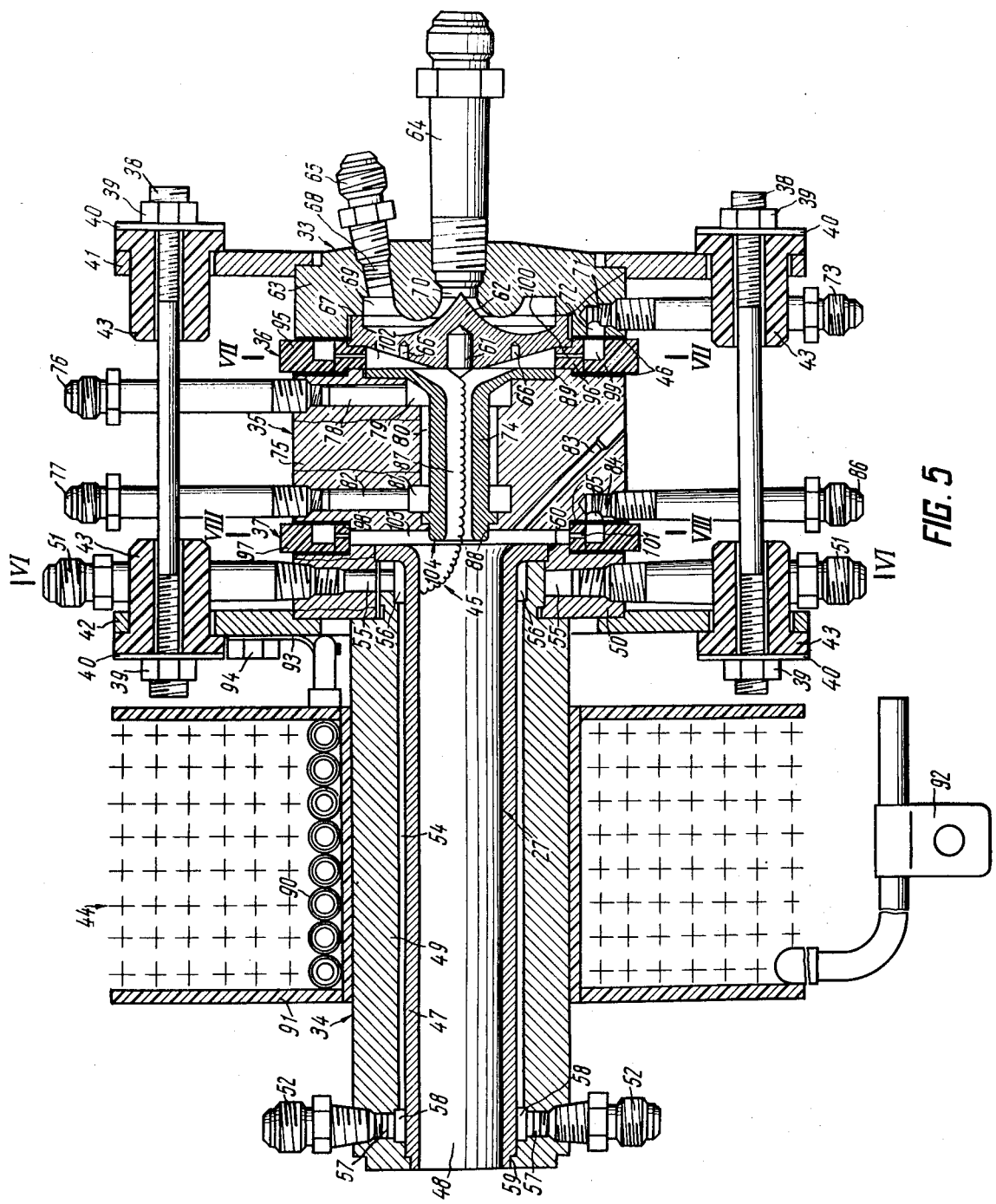
FIG. 5 is a longitudinal section of an electric-arc plasmochemical reactor of a unidirectional-discharge type.

A possible design of an apparatus embodying the proposed method of heating gas is given in FIG. 5. The unidirectional-discharge electric-arc plasmochemical reactor 27 comprises a rod-type electrode (usually a cathode) 33 and a hollow cylindrical electrode (usually an anode) 34. Intermediate the electrodes 33 and 34 there is disposed a hollow cylindrical diaphragm 35 which adjoins the rod-type electrode 33 through an insulating heat carrier gas inlet conduit 36 and also adjoins the cylindrical electrode 34 through an insulating stock gas inlet conduit 37.

The foregoing elements are fastened by dowels 38, nuts 39, washers 40 and flange couplings 41 and 42 constructed from an electrically conductive material. There is a terminal (not shown in the drawing) on the flange coupling 41 provided for electrical connection to a source of power supply. Bushes 43 serve to insulate the electrodes 33 and 34. A solenoid 44 is disposed on the cylindrical electrode 34. An electric arc 45 is energized across the electrodes 33 and 34. Gaskets 46 are provided for sealing purposes.

The cylindrical electrode 34 comprises a bush 47 (FIGS. 5 and 6) constructed from an electrically conductive material and making electrical connection to the electric arc 45, the chemical reactions taking place within an inner cavity 48 of the bush 47, a housing 49 constructed from a non-ferromagnetic material, e.g. brass, a flange coupling 50 constructed from an electrically conductive material, connecting pipes 51 wherethrough cooling water is supplied, and connecting pipes 52 (FIG. 5) wherethrough cooling water is discharged. A space 54 for cooling water is provided between the bush 47 and the housing 49. Conduits 55, 56 (FIGS. 5 and 6) and 57 and 58 (FIG. 5) provide passage means for cooling water. The bush 47 (FIG. 5) is joined to the housing 49 and the flange coupling 50 by means of soldered joints 59 and 60.

The rod-type electrode 33 comprises a rod 61 contacting the electric arc 45 and constructed from a high-melting electrically conductive material, e.g. tungsten, an electrically conductive plate 62, with the rod 61 being press-fitted thereinto, an electrically conductive housing 63 threadedly receiving the plate 62, a connecting pipe 64 for supplying cooling water and a connecting pipe 65 for discharging cooling water. Keyholes 66 are provided in the plate 62. Gaskets 67 serve for sealing purposes. Conduits 68, 69 and 70 provide passage means for cooling water. Openings 71 and 72 are formed in the housing 43 for the purpose of supplying the intermediate heat carrier gas to the insulating inlet conduit 36. A connecting pipe 73 coupled to an insulating gas-supply hose (not shown in the drawing) serves the same purpose.

The hollow cylindrical diaphragm 35 is formed on the same general lines as the cylindrical electrode 34. It comprises a bush 74 constructed from a highly thermally conductive material, e.g. copper (FIG. 5), a housing 75, connecting pipes 76 for supplying cooling water, and conduits 78–82 providing passage means for cooling water. An opening 83 for measuring the pressure inside the electrode 34 and openings 84 and 85 for supplying the stock gas to be heated to the insulating stock gas inlet conduit 37 are formed in the housing 75. A connecting pipe 86 serves as a means of coupling with a gas-supply hose (not shown in the figure). A conduit 87 provides a passage means for the intermediate heat carrier gas flow heated by the electric arc 45. Soldered joints 88 and 89 connect the bush 74 to the housing 75.

The solenoid 44 comprises an electrically conductive (brass or copper) circular-section tube 90 wound upon a framework 91 constructed from an electric-insulating material. Welded onto the ends of the tube 90 are terminals 92 and 93 whereby the solenoid 44 can be connected to a source of power supply (not shown in the figure) and to the flange coupling 42, respectively, the terminal 93 being secured to the flange 42 by means of a screw 94.

Figure 7:
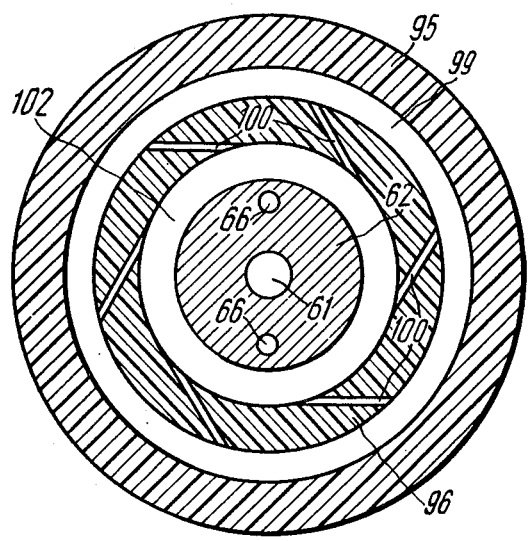
FIG. 7 is the view of FIG. 5 taken on the line VI—VI.

Each insulating inlet conduit 36 and 37 comprises two portions, 95, 96 (FIGS. 5 and 7) and 97,98 (FIGS. 5 and 8), respectively, which are so constructed as to define gas-distributing annular conduits 99 and 100 (FIGS. 5 and 7). Conduits 100 (FIGS. 5 and 7) and 101 (FIGS. 5 and 8) serve to supply the intermediate heat carrier gas and the stock gas to be heated to spaces 102 (FIGS. 5 and 7) and 103 (FIGS. 5 and 8), respectively, as well as for rotating the streams of said gases. The protruding portion of the bush 74 indicated at 104 in FIG. 5 is intended to change the direction of flow of the stock gas being heated.

Figure 9:
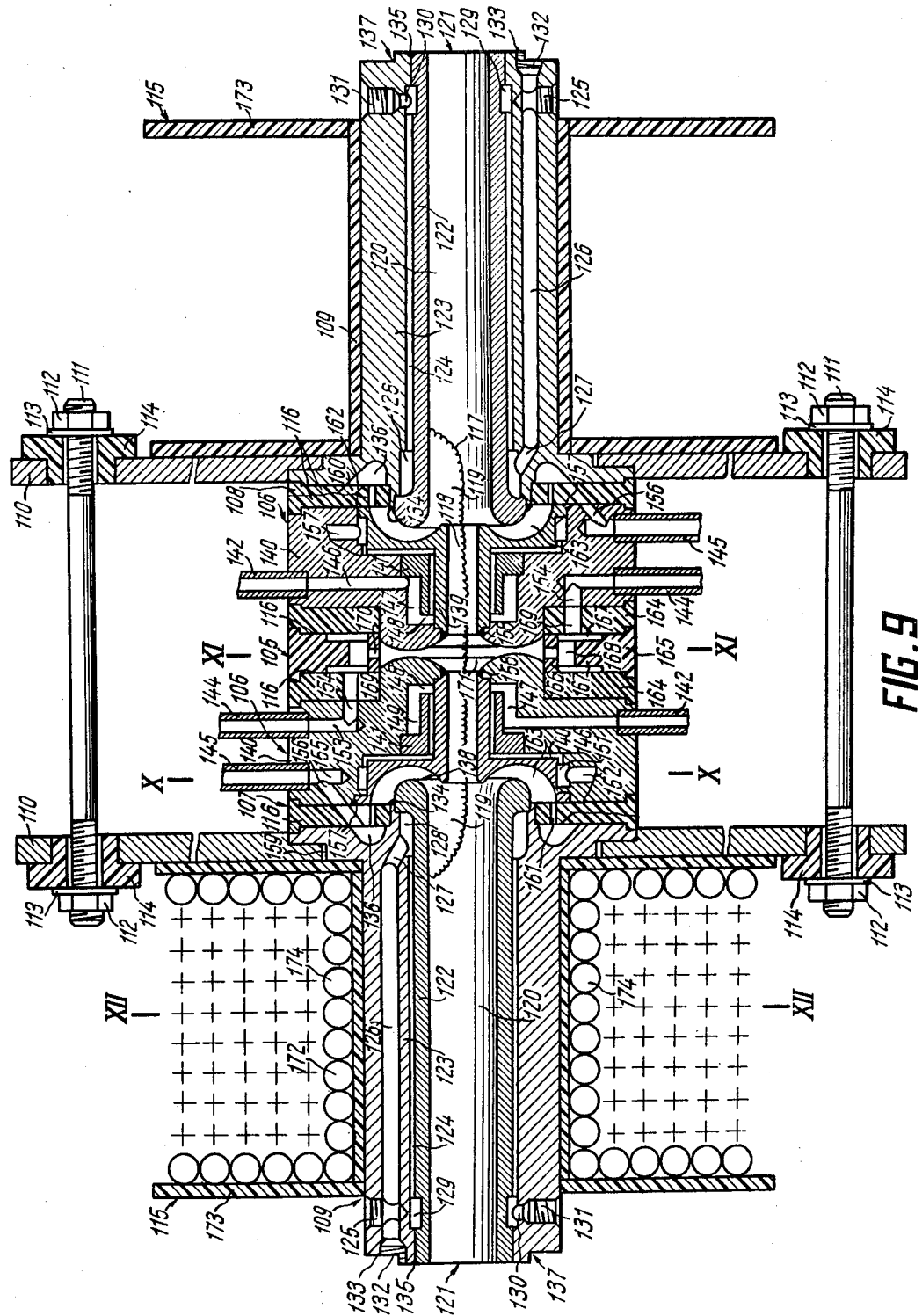
FIG. 9 is a longitudinal section of an alternative embodiment of an electric-arc plasmochemical reactor wherein the heated gas is discharged in two opposite directions.

The electric-arc plasmochemical reactor shown in longitudinal section in FIG. 9 is a two-way gas-discharge arrangement, comprising an insulating ring 105 positioned symmetrically in relation to the entire reactor and designed as inlet means for the intermediate heat carrier gas. Jointed with the ring 105 are two hollow cylindrical diaphragms 106 which are coupled with two hollow cylindrical electrodes 109 by way of stock gas inlet rings 107 and 108. All the above elements are united by two flange couplings 110, six dowels 111, nuts 112 and washers 113. Bushes 114 insulate the electrodes 109. Solenoids 115 are fitted over the electrodes 119, gaskets 116 serving as sealing members. An electric arc 117 is energized in inner cavities 108 of the diaphragms 106 and in inner cavities 119 of the electrodes 109 disposed proximately to the diaphragms 106. The remaining inner space of the electrodes 109 beyond the terminal portion of the arc and indicated at 120 is employed as a reaction space. The heated gas is discharged through openings 121.

The electrode 109 comprises a bush 122 constructed from an electrically conductive material and a housing 123 constructed from a non-ferromagnetic material. A space 124 is provided between the bush 122 and the housing 123 for cooling water.

Water is supplied to the space 124 through a hole 125 threadedly receiving an inlet connection (not shown in the drawing), conduits 126 and 127 and an annular conduit 128. Water is discharged through an annular conduit 129, a conduit 130 and a hole 131 threadedly receiving an outlet connection (not shown in the drawing). The conduit 126 is stoppered by a plug 132 screwed into the housing 123. Having been screwed into place, the plug 132 is held fast by a sealing heel 133. The bush 122 is also joined with the housing 123 by means of tight soldered joints 134 and 135. There is an annular recess 136 formed in the housing 123 to provide for the passage of the stock gas to be heated and a centering annular projection 137 for coupling with a quenching member (not shown in the drawing). An annular projection 138 is designed to protect the ring 107 from the effluent stream of heated intermediate heat carrier gas discharged from the diaphragm 106.

Figure 6:
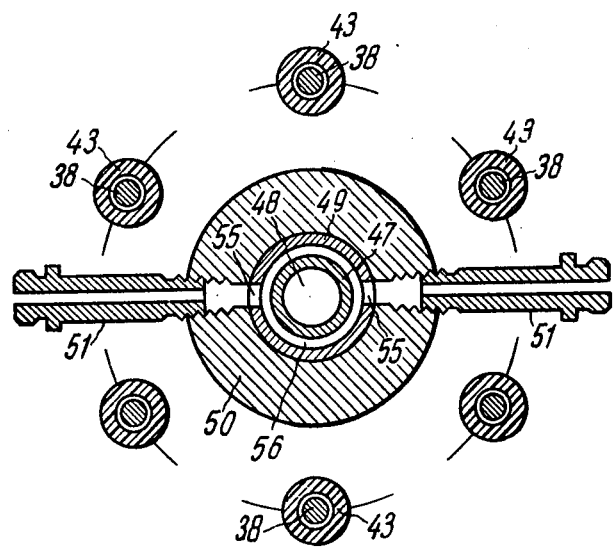
FIG. 6 is the view of FIG. 5 taken on the line V—V.
Figure 11:
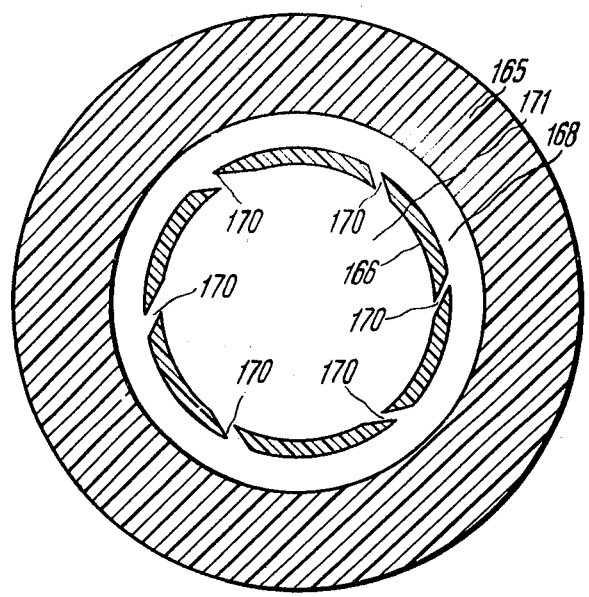
FIG. 11 is the view of FIG. 9 taken on the line X—X.

The diaphragm 106 comprises a bush 139 constructed from a highly thermally conductive material (e.g. copper), a housing 140 constructed from a non-ferromagnetic material, an insert 141, a cooling water inlet branch pipe 142, a cooling water outlet branch pipe 143 (FIG. 11), an intermediate heat carrier gas inlet branch pipe 144 (FIG. 9), and a stock gas inlet branch pipe 145 (FIGS. 9 and 11), all the branch pipes 142-145 being soldered into the housing 140 (FIG. 6).

Cooling water blows through conduits 146-148, a space 149 and conduits 150-152, the intermediate heat carrier gas is supplied through conduits 153 and 154, and the stock gas to be heated is supplied through conduits 155 and 156.

The bush 139 is hermetically jointed with the housing 140 by means of soldered joints 157 and 158.

Figure 10:
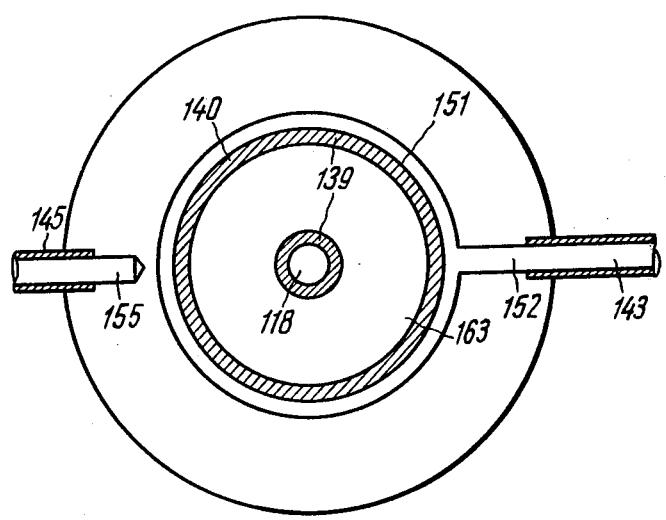
FIG. 10 is the view of FIG. 9 taken on the line IX—IX.

Passages 159 and 160 are formed in the insulating rings 107 and 108 for the stock gas to be heated. Openings 161 and 162 are also provided in the insulating rings 107 and 108 wherethrough the stock gas to be heated is admitted into a space 163 (FIGS. 9 and 10).

The insulating ring 105 (FIG. 9) incorporates rings 164–166, with passages 167 and 168 defined therebetween to allow the flow of the intermediate heat carrier gas. The ring 164 has a passage 169 for the heat carrier gas, while the ring 166 gas openings 170 (FIGS. 9 and 11) wherethrough the heat carrier gas is forced into a space 171.

Figure 12:
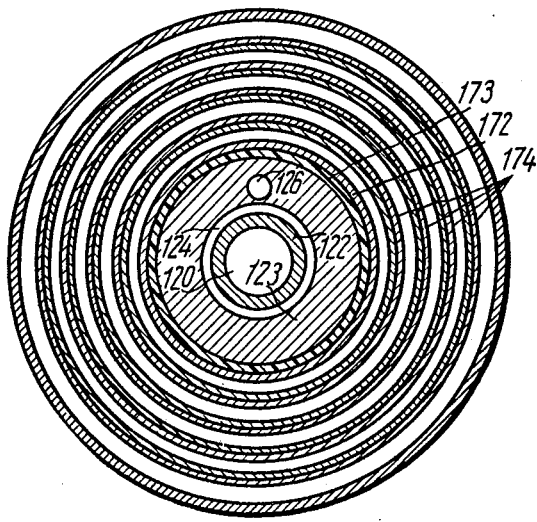
FIG. 12 is the view of FIG. 9 taken on the line XI—XI.

The solenoid 115 (FIG. 9) comprises an electrically conductive tube 172 (FIGS. 9 and 12) wound upon a framework 173 constructed from an electric-insulating material. On one end of the tube 172 there is provided a terminal (not shown in the drawing) for electrical connection to a source of power supply (not shown in the drawing), whereas the other end of the tube 172 is coupled to the electrode 109 (the connection is not shown in the drawing). Both ends of the tube 172 are likewise provided with connecting pipes (not shown in the drawing) wherethrough cooling water is supplied and discharged. Insulation 174 is provided between the layers of the tube 172.

The method of the present invention is realized as follows.

An intermediate heat carrier gas is introduced into the electric-arc plasmochemical reactor through the inlet means 3 (FIG. 1) and passes along the rotary electric arc 6 across the electrodes 1 and 2.

The type of heat carrier depends on the particular process. Thus, in the production of acetylene from hydrocarbons, the intermediate heat carrier may be chlorine, hydrogen chloride, carbon dioxide, inert gases, nitrogen, air, hydrogen, water vapor, or mixtures of the above gases. The most advantageous intermediate heat carrier in this case is hydrogen for it is formed in the course of hydrocarbon pyrolysis so that the subsequent recovery of the desired product is simplified. All intermediate heat carriers rarely the reacted gas, but inert gases offer an advantage of forming no by-products. However, should it be required that the reacted gas contains a certain level of carbon oxides (for example, synthesis gas to produce methanol) water vapor or carbon dioxide can be employed as the intermediate heat carrier.

For the production of synthesis gas to manufacture vinyl chloride, the intermediate heat carrier may be chlorine, hydrogen chloride or mixtures thereof with hydrogen.

Nitrogen is the most convenient intermediate heat carrier for the production of hydrogen cyanide from hydrocarbons. In this case air is likewise suitable, but its oxygen will give by-products.

Air is the most suitable intermediate heat carrier for nitrogen oxide production, but nitrogen, oxygen or carbon dioxide are likewise applicable.

The stock gas to be heated is introduced through the inlet means 4, mixed with the heated intermediate heat carrier gas, and the resultant mixture is additionally heated by the rotary electric arc 6. The portion of the electrode 2 disposed beyond the arc 6 is employed as a reaction space wherein the heated mixture undergoes chemical transformations. The reacted gas from the electrode 2 is discharged through the discharge orifice 5 into a quenching member (not shown in the figure) wherein the desired products formed at high temperature are fixed.

The stock gas to be heated may be represented by a variety of gaseous or vaporous substances. Thus, for example, in the production of acetylene, hydrogen cyanide as well as synthesis gases for vinyl chloride or methanol, any gaseous or prevaporized fluid hydrocarbon will serve the purpose; whereas in the oxidation of nitrogen, the stock gas, depending on the kind of intermediate heat carrier employed, may be oxygen, nitrogen, carbon dioxide or air.

The intermediate heat carrier gas plasma jet is produced through heating the gas with the electric arc 9 (FIG. 2) after the gas is injected through the inlet means 10. The plasma jet is supplied to the hollow electrode 13 wherein it is additionally heated by the electric arc 11 together with the gas supplied through the orifice 14 for heating.

In order to prolong the service life of the installation, the required power is desirably obtained at a high voltage and a minimum current. This can be achieved by elongating the portion 22 (FIG. 3) of the arc 6 (FIG. 1) in the diaphragm 20 (FIG. 3) and improving the conditions of blowing thereof. To this end, the stream of intermediate heat carrier is desirably rotated so that the arc portion 22 is blown with a swirling stream. The intermediate heat carrier stream is rotated by the inlet means 24 provided with tangential heat openings.

The swirling stream of intermediate heat carrier rotates the terminal portion 23 of the electric arc 22, with the result that the service life of the electrodes is prolonged and the stock gas being heated is more effectively mixed with the intermediate heat carrier. Rotation of the portion 23 of the electric arc is likewise attainable by rotating the stock gas stream in the inlet means 26, or utilizing the combined effect of the rotational streams of both gases.

The intermediate heat carrier and the stock gas streams can be rotated both in the same direction and on the counterflow principle, the latter technique conducive to a more effective mixing of said gases.

The service life of the electrode 19 increases with an increase in the surface area covered by the running arc spot as the terminal portion 23 of the electric arc is rotating. It is preferable, therefore, that the electrode 19 should have a larger diameter as compared with the diaphragm 20. In such a case, the stock gas to be heated is introduced beyond the diaphragm 20 at the initial portion of the electrode 19. The arc portion 23 in the larger-diameter electrode 19 is the more effectively rotated by a rotational flow of the stock gas being heated.

If the stock gas to be heated is to be more effectively mixed with the intermediate heat carrier, the rotation of the arc portion 23 should preferably be intensified by the effect of a magnetic field directed along the axis of the electrode 19. This can be achieved by mounting the solenoid 21 on the electrode 19, the solenoid 21 being either coupled in series with the arc 22 or supplied from an independent source. A permanent magnet or a superconducting circuit can likewise be employed to the same end. The arc may be rotated by the magnetic field either in the direction of rotation of the intermediate heat carrier or the stock gas to be heated, or else in the opposite direction. The speed of rotation of the arc portion 23 must be such that the gases are mixed faster than the reaction time; as a rule, the arc portion 23 rotates at from $10^3$ to $10^4$ revolutions per second.

The temperature of the heated intermediate heat carrier at the outlet of the diaphragm 20 depends on the type of process. Thus, for example, in the production of acetylene from natural gas with hydrogen being employed as the intermediate heat carrier, hydrogen is heated to 3,000° to 4,000° K. The temperature of the mixture at the outlet 25 of the reaction space likewise depends on the type of process, being within 1,300° to 2,000° K. in the process of acetylene production from methane.

In order to effect a process of arc heating of chemically reactant gases, the required elements are the electric arc plasmochemical reactor 27 (FIG. 4), the source of power supply 28 providing for a stable arc 6 (FIG. 1) and current control feature for the electric-arc plasmochemical reactor 27 (FIG. 4). The gas-supply source 29 supplies an intermediate heat carrier and a stock gas to the electric-arc plasmochemical reactor 27 and also stabilizes and controls the requisite parameters of said gases. The auxiliary system 30 is designed to control the installation, measure all the parameters and supply cooling water to the electric-arc plasmochemical reactor 27.

From the electric-arc plasmochemical reactor 27 the reacted gases are delivered to the quenching member 31 wherein they are sharply cooled (quenched) by any known method to a temperature at which the desired product which has formed at high temperature in the electric-arc plasmochemical reactor 27, ceases decomposing. From the quenching member 31 the gas is delivered to the system 32 for recovery of the desired product. Said system 32 may incorporate a component device for the recovery, by any known method, of the waste-heat of the gases effluent from the quenching member 31, thereby raising the efficiency of the process.

Gas heating in the electric-arc plasmochemical reactor of a unidirectional-discharge type as shown in FIG. 5 is effected as described hereinabove. Through the connecting pipe 73 and the openings 71 and 72 the intermediate heat carrier is fed into the conduit 99 of the insulating inlet 36. From the conduit 99 the intermediate heat carrier flows through a system of tangential openings 100 (FIGS. 5 and 7) and into the space 102 (FIG. 5) between the diaphragm 35 and the rod-type electrode 33. Then the rotational stream of the intermediate heat carrier flows along the conduit 87 of the diaphragm 35, blowing the arc 45 to be heated thereby and escapes into the inner cavity 48 of the electrode 34.

Figure 8:
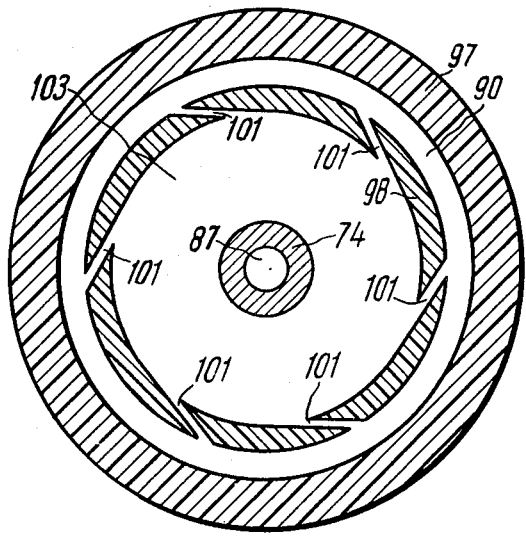
FIG. 8 is the view of FIG. 5 taken on the line VII—VII.

The stock gas to be heated is supplied to the conduit 100 of the insulating inlet 37 through the connecting pipe 86 and the conduits 84 and 85, wherefrom the stock gas flows into the space 103 (FIG. 5) between the diaphragm 35 and the electrode 34 through a system of tangential openings 101 (FIGS. 5 and 8). An alternative embodiment of the present invention has also been developed (not shown in the drawings) wherein the stock gas to be heated is not rotated but is introduced through a system of radial openings.

In the initial portion of the inner cavity 48 of the electrode 34 the stock gas being heated is mixed with the heated intermediate heat carrier effluent from the conduit 87 of the diaphragm 35. The mixing of said gases is intensified by the terminal portion of the electric arc 45 rotating in a magnetic field set up by the solenoid 44 which is connected in series with the arc 45. The rotating terminal portion of the arc 45 also additionally heats the mixture of the stock gas with the intermediate heat carrier.

Having passed through the rotating terminal portion of the arc 45, the heated mixture flows through the inner cavity of the electrode 34 where chemical reactions take place. At the outlet of the electrode 34 the reacted mixture is delivered to a quenching member (not shown in the figure).

The hollow cylindrical electrode 34 is cooled by water which flows through the connecting pipes 51 and conduits 55 and 56 into the space 54. Flowing through the space 44 cooling water cools the bush 47 heated by the arc spot and by the hot gas mixture. From the space 54 the heated water is discharged from the electrode 34 through the conduits 57 and 58 and out through the connecting pipes 52.

The diaphragm 35 is cooled in a similar manner. Through the connecting pipe 76 and conduits 78 and 79 water is delivered into the space 80 and passes therethrough, cooling and bush 74 being heated by the hot intermediate heat carrier as well as by the heat emission of the arc 45. The heated water is discharged from the space 80 of the diaphragm 35 through the conduits 81 and 82 and out through the connecting pipe 77.

The heat flux from the high-melting rod 61 heated by the arc 45 is removed through the plate 62 to cooling water which is fed into the space 69 defined by the plate 62 and the housing 63 through the connecting pipe 64 and the conduit 70. From the space 69 the heated water is discharged from the electrode 33 through the conduit 68 and out through the connecting pipe 65.

Electric current is supplied from the positive pole of a power supply source (not shown in the figure) to the terminal 92 of the solenoid 44, wherefrom it flows to the bush 47 of the electroded 44 via the terminal 93, the flange coupling 42 and the flange coupling 50 of the electrode 34. Then, via the electric arc 45, current flows to the rod 61 of the electrode 33, then through the plate 62 and the housing 63 of the electrode 33 to the flange coupling 41 whereon is disposed a negative terminal (not shown in the drawing) coupled to the source of power supply (not shown in the figure).

The electric-arc plasmochemical reactor according to the present invention can likewise be supplied from an a-c source using any known method of maintaining the arc energized as current passes through zero in case an industrial frequency is used. The two-way discharge electric-arc plasmochemical reactor shown in FIG. 9 receives intermediate heat carrier through two branch pipes 144 wherefrom it flows through the conduits 153 and 154 disposed in the housings 140 of the diaphragms 106 into the passages 169, 167 and 168 formed in the insulating ring 105. From the annular passage 168 the intermediate heat carrier is delivered, through a system of tangential openings 170 (FIGS. 9 and 11), into the space 171 (FIG. 9) defined by the diaphragm 106, wherefrom the eddying gas stream flows symmetrically both ways through the inner cavities 118 of the diaphragms 106, blowing the arc 117. The intermediate heat carrier heated by the arc 117 flows from the spaces 118 of the diaphragms 106 into the space 119 of the initial portions of the electrodes 109 adjoining the diaphragms 106.

The stock gas flows through two branch pipes 145, the conduits 155 and 156 disposed in the housings 140 of the diaphragms 106 and the passages 159 and 160 formed in the insulating rings 107 and 108 and into the annular spaces 136 defined by the recesses formed in the housings 123 of the electrodes 109. From the annular recesses 136 through a system of openings 161 and 162 the stock gas flows into the spaces 163 defined by the electrodes 109 and the diaphragms 106. The openings 161 and 162 are so oriented in each of the insulating rings 107 and 108 as to rotate both streams of stock gas in a single eddy directed either along and oppositely the eddy of the intermediate heat carrier. The direction of the eddying streams can be changed by reorienting the position of the insulating ring 105 and/or by interchanging the positions of the insulating rings 107 and 108. From the spaces 163 the stock gas being heated flows into the initial inner cavities 119 of the electrodes 109 to be mixed therewithin with the heated intermediate heat carrier effluent from the cavities 118 of the diaphragms 106.

Passing through the rotating terminal portions of the arc 117, the gas mixture is additionally heated to a higher temperature. Rotation of the terminal portions of the arc 117 induced by the current of the arc 117 cooperating with the magnetic field of the solenoids 115 improves the effectiveness of mixing of the stock gas being heated with the heated intermediate heat carrier. Leaving the zone of rotation of the terminal portions of the arc 117, the heated mixture of gases enters the inner spaces 120 of the electrodes 109 where chemical reactions taken place. The reacted mixture is delivered through the openings 121 of the electrodes 109 to the quenching members not shown in the drawing.

Cooling water enters the electrodes 109 through the holes 125, flows through the conduits 126 (FIGS. 9 and 12) along the housings 123 of the electrodes 109 (FIG. 9) into the conduits 127 and 128. From the annular conduits 128 cooling water enters the spaces 124 and, flowing therethrough, cools the bushes 122 being heated by the hot gas mixture as well as by the arc spots. The heated water is discharged from the electrodes 109 from the spaces 124 through the conduits 129 and 130, through the hole 131 and out.

Water enters the diaphragms 106 through the branch pipes 142, wherefrom it flows through the conduits 146, 147 and 148 into the spaces 149 and flows therethrough, cooling and bushes 139 being heated by the hot intermediate heat carrier and by the heat emission of the arc 117. Leaving the spaces 149, the heated water flows through the conduits 150, 151 and 152 into the branch pipes 153 (FIG. 10) wherethrough it is discharged from the diaphragms 106 (FIG. 9).

Electric current flows from the input terminals (not shown in the drawing) located on the ends of the tubes 172 of the solenoids 115 through the tubes 172 of the solenoids 115, the terminals (not shown in the drawing) located on the other ends of the tubes 172 of the solenoids 115 and the terminals (not shown in the drawing) located on the other ends of the tubes 172 of the solenoids 115 and coupled to the housings 123 of the electrodes 109, through said housings 123 and to the bushes 122 of the electrodes 109 which are in contact with the electric arc 117.

What is claimed is:

1. A method of producing a synthesis gas for the manufacture of vinyl chloride which comprises feeding a gaseous or vaporized hydrocarbon into an intermediate gas plasma jet, said intermediate gas plasma jet being selected from the group consisting of chlorine, hydrogen chloride and mixtures thereof with hydrogen, and mixing the hydrocarbon with the intermediate gas plasma jet to heat the hydrocarbon by a rotary electric arc supplying additional heat to the gas and said gas plasma jet by said rotary electric arc.

2. A method as claimed in claim 1, whereby said intermediate gas plasma jet is produced by heating said gas with an electric arc connected in series with said rotary electric arc.

3. A method as claimed in claim 2, wherein said rotary electric arc and the arc for heating the intermediate gas are combined as a single electric arc.

4. A method as claimed in claim 1, wherein the electric arc is rotated by blowing said arc with a swirling jet of intermediate heat carrier gas.

5. A method as claimed in claim 1, wherein the electric arc is rotated by a swirling jet of gas to be heated.

6. A method as claimed in claim 1, wherein the electric arc is rotated by a magnetic field.

7. A method as claimed in claim 4, wherein the electric arc is rotated additionally by a magnetic field.

8. A method as claimed in claim 5, wherein the electric arc is rotated by a magnetic field.

* * * * *